US006630075B2

(12) United States Patent
Behr et al.

(10) Patent No.: US 6,630,075 B2
(45) Date of Patent: Oct. 7, 2003

(54) USE OF FLUORINATED KETONES IN FIRE EXTINGUISHING COMPOSITIONS

(75) Inventors: Fred E. Behr, Woodbury, MN (US); Daniel R. Vitcak, Cottage Grove, MN (US); Richard M. Flynn, Mahtomedi, MN (US); Michael G. Costello, Afton, MN (US); Michael J. Parent, Oakdale, MN (US); Zhongxing Zhang, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/269,179

(22) Filed: Oct. 11, 2002

(65) Prior Publication Data

US 2003/0089877 A1 May 15, 2003

Related U.S. Application Data

(62) Division of application No. 09/619,306, filed on Jul. 19, 2000, now Pat. No. 6,478,979.

(60) Provisional application No. 60/144,760, filed on Jul. 20, 1999.

(51) Int. Cl.[7] ................................................ C07C 49/04

(52) U.S. Cl. .................. 252/183.11; 568/338; 568/340; 568/342; 568/385; 568/410; 568/419

(58) Field of Search ..................... 252/183.11; 568/338, 568/340, 342, 385, 410, 419

(56) References Cited

U.S. PATENT DOCUMENTS

| | | | |
|---|---|---|---|
| 3,185,734 A | 5/1965 | Fawcett et al. | |
| 4,136,121 A | 1/1979 | Martini et al. | |
| 5,040,609 A | 8/1991 | Dougherty et al. | |
| 5,084,190 A | 1/1992 | Fernandez | |
| 5,115,868 A | 5/1992 | Dougherty, Jr. et al. | |
| 5,117,917 A | 6/1992 | Robin et al. | |
| 5,124,053 A | 6/1992 | Iikubo et al. | |
| 5,141,654 A | 8/1992 | Fernandez | |
| 5,247,101 A | 9/1993 | Takago et al. | |
| 5,250,200 A | 10/1993 | Sallet | |
| 5,399,718 A | 3/1995 | Costello et al. | |
| 5,444,102 A | 8/1995 | Nimitz et al. | |
| 5,457,238 A | 10/1995 | Petrov et al. | |
| 5,466,877 A | 11/1995 | Moore et al. | |
| 5,476,974 A | 12/1995 | Moore et al. | |
| 5,488,142 A | 1/1996 | Fall et al. | |
| 5,718,293 A | 2/1998 | Flynn et al. | |
| 5,998,671 A | 12/1999 | Van Der Puy | |
| 6,403,149 B1 * | 6/2002 | Parent et al. | 427/130 |

FOREIGN PATENT DOCUMENTS

| | | |
|---|---|---|
| JP | 2893038 B1 | 5/1999 |
| SU | 698289 | 2/1985 |
| WO | 98/19742 | 5/1998 |

OTHER PUBLICATIONS

P.S. Zurer, "Looming Ban on Production of CFCs, Halons Spurs Switch to Substitutes," Chemical & Engineering News, Nov. 15, 1993, pp. 12–18.

S.O. Andersen et al., "Halons, Stratospheric Ozone and the U.S. Air Force," The Military Engineer, Aug., 1988, vol. 80, No. 523, pp. 485–492.

US Navy Halon 1211 Replacement Plant Part 1—Development of Halon 1211 Alternatives, Nov. 1, 1999, Naval Research Lab, Washington, D.C.

R.D. Smith et al., "The Chemistry of Carbonyl Fluoride. II. Synthesis of Perfluoroisopropyl Ketones," Journal of American Chemical Society, v. 84, pp. 4285–4288, 1962.

ASTM E681–1998 ( update of E681–85) Standard Test Method for Concentration Limits of Flammability of Chemicals (Vapors and Gases), 1998.

NFPA 2001, "Standard for Clean Agent Fire Extinguishing Systems," 2000 Edition, Table 1–5.1.2, p. 2001–5:2000.

Chemical Abstracts, vol. 82, Apr. 14–Apr. 28 (Abstracts 92724–112252), p. 406, published by the American Chemical Society (1975).

* cited by examiner

*Primary Examiner*—Cephia D. Toomer

(57) ABSTRACT

Fire extinguishing compositions and methods for extinguishing, controlling, or preventing fires are described wherein the extinguishing agent is a fluorinated ketone having up to two hydrogen atoms, alone, or in admixture with a co-extinguishing agent selected from hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, iodofluorocarbons, hydrobromofluorocarbons, and mixtures thereof.

4 Claims, No Drawings

USE OF FLUORINATED KETONES IN FIRE EXTINGUISHING COMPOSITIONS

CROSS-REFERENCE TO RELATED APPLICATIONS

This application is a divisional of U.S. application Ser. No. 09/619,306, filed Jul. 19, 2000, now U.S. Pat. No. 6,478,979; which claims priority to U.S. Provisional Patent Application Serial No. 60/144,760 filed Jul. 20, 1999.

FIELD OF THE INVENTION

This invention relates to fire extinguishing compositions comprising at least one fluorinated ketone compound and to processes for extinguishing, controlling, or preventing fires using such compositions, for making alpha-branched fluorinated ketones, and for purifying such ketones.

BACKGROUND OF THE INVENTION

Various different agents and methods of fire extinguishing are known and can be selected for a particular fire, depending upon its size and location, the type of combustible materials involved, etc. Halogenated hydrocarbon fire extinguishing agents have traditionally been utilized in flooding applications protecting fixed enclosures (e.g., computer rooms, storage vaults, telecommunications switching gear rooms, libraries, document archives, petroleum pipeline pumping stations, and the like), or in streaming applications requiring rapid extinguishing (e.g., military flight lines, commercial hand-held extinguishers, or fixed system local application). Such extinguishing agents are not only effective but, unlike water, also function as "clean extinguishing agents," causing little, if any, damage to the enclosure or its contents.

The most commonly-used halogenated hydrocarbon extinguishing agents have been bromine-containing compounds, e.g., bromotrifluoromethane ($CF_3Br$, Halon™ 1301) and bromochlorodifluoromethane ($CF_2ClBr$, Halon™ 1211). Such bromine-containing halocarbons are highly effective in extinguishing fires and can be dispensed either from portable streaming equipment or from an automatic room flooding system activated either manually or by some method of fire detection. However, these compounds have been linked to ozone depletion. The Montreal Protocol and its attendant amendments have mandated that Halon™ 1211 and 1301 production be discontinued (see, e.g., P. S. Zurer, "Looming Ban on Production of CFCs, Halons Spurs Switch to Substitutes," *Chemical & Engineering News*, page 12, Nov. 15, 1993).

Thus, there has developed a need in the art for substitutes or replacements for the commonly-used, bromine-containing fire extinguishing agents. Such substitutes should have a low ozone depletion potential; should have the ability to extinguish, control, or prevent fires or flames, e.g., Class A (trash, wood, or paper), Class B (flammable liquids or greases), and/or Class C (electrical equipment) fires; and should be "clean extinguishing agents," i.e., be electrically non-conducting, volatile or gaseous, and leave no residue. Preferably, substitutes will also be low in toxicity, not form flammable mixtures in air, have acceptable thermal and chemical stability for use in extinguishing applications, and have short atmospheric lifetimes and low global warming potentials. The urgency to replace bromofluorocarbon fire extinguishing compositions is especially strong in the U.S. military (see, e.g., S. O. Andersen et al., "Halons, Stratospheric Ozone and the U.S. Air Force," *The Military Engineer*, Vol. 80, No. 523, pp. 485–492, August, 1988). This urgency has continued throughout the 1990s (see *US Navy Halon 1211 Replacement Plan Part 1—Development of Halon 1211 Alternatives*, Naval Research Lab, Washington, D.C., Nov. 1, 1999).

Various different fluorinated hydrocarbons have been suggested for use as fire extinguishing agents. However, to date, we are unaware that any fluorinated ketone having zero, one, or two hydrogen atoms on the carbon backbone has been evaluated as a fire-fighting composition.

SUMMARY OF THE INVENTION

In one aspect, this invention provides a process for controlling or extinguishing fires. The process comprises introducing to a fire or flame (e.g., by streaming or by flooding) a non-flammable extinguishing composition comprising at least one fluorinated ketone compound containing up to two hydrogen atoms. Preferably, the extinguishing composition is introduced in an amount sufficient to extinguish the fire or flame. The fluorinated ketone compound can optionally contain one or more catenated (i.e., "in-chain") oxygen, nitrogen or sulfur heteroatoms and preferably has a boiling point in the range of from about 0° C. to about 150° C.

The fluorinated ketone compounds used in the process of the invention are surprisingly effective in extinguishing fires or flames while leaving no residue (i.e., function as clean extinguishing agents). The compounds can be low in toxicity and flammability, have no or very low ozone depletion potentials, and have short atmospheric lifetimes and low global warming potentials relative to bromofluorocarbons, bromochlorofluorocarbons, and many substitutes therefor (e.g., hydrochlorofluorocarbons, hydrofluorocarbons, and perfluorocarbons). Since the compounds exhibit good extinguishing capabilities and are also environmentally acceptable, they satisfy the need for substitutes or replacements for the commonly-used bromine-containing fire extinguishing agents which have been linked to the destruction of the earth's ozone layer.

In other aspects, this invention also provides an extinguishing composition and a process for preventing fires in enclosed areas.

The present invention also provides novel fluoroketones of the formula $(CF_3)_2CFC(O)CF_2Cl$ and $CF_3OCF_2CF_2C(O)CF(CF_3)_2$ and fire extinguishing compositions which include such novel fluoroketones in amounts sufficient to extinguish a fire.

The present invention also provides a process for reacting an acyl halide with hexafluoropropylene to make a fluorinated ketone having a minimal amount of dimer and trimer by-products.

The present invention further provides a process for removing undesired dimeric and/or trimeric by-products formed in the preparation of a fluorinated ketone prepared by the reaction of hexafluoropropylene with an acyl halide in the presence of fluoride ion where the reaction product, i.e., the fluorinated ketone, is treated with an alkali permanganate salt, e.g. potassium permanganate, in a suitable solvent.

DETAILED DESCRIPTION OF ILLUSTRATIVE EMBODIMENTS OF THE INVENTION

Compounds that can be utilized in the processes and composition of the invention are fluorinated ketone compounds. The compounds of this invention can be utilized alone, in combination with one another, or in combination with other known extinguishing agents (e.g., hydrofluorocarbons, hydrochlorofluorocarbons, perfluorocarbons, perfluoropolyethers, hydrofluoropolyethers, hydrofluoroethers, chlorofluorocarbons, bromofluorocarbons, bromochlorofluorocarbons, hydrobromocarbons, iodofluorocarbons, and hydrobromofluorocarbons). The compounds can be solids, liquids, or gases under ambient conditions of temperature and pressure, but are preferably utilized for extinguishing in either the liquid or the vapor state (or both). Thus, normally solid compounds are preferably utilized after transformation to liquid and/or vapor through melting, sublimation, or dissolution in a liquid co-extinguishing agent. Such transformation can occur upon exposure of the compound to the heat of a fire or flame.

Fluorinated ketones useful in this invention are ketones which are fully fluorinated, i.e., all of the hydrogen atoms in the carbon backbone have been replaced with fluorine; or ketones which are fully fluorinated except for one or two hydrogen, chlorine, bromine and/or iodine atoms remaining on the carbon backbone. Fire performance is compromised when too many hydrogen atoms are present on the carbon backbone. For example, a fluorinated ketone with three or more hydrogen atoms on the carbon backbone performs more poorly than a ketone with the same fluorinated carbon backbone but having two, one or zero hydrogen atoms, so that significantly more extinguishing composition of the former is required to extinguish a given fire. The fluoroketones may also include those that contain one or more catenated heteroatoms interrupting the carbon backbone in the perfluorinated portion of the molecule. A catenated heteroatom is, for example, a nitrogen, oxygen or sulfur atom.

Preferably, the majority of halogen atoms attached to the carbon backbone are fluorine; most preferably, all of the halogen atoms are fluorine so that the ketone is a perfluorinated ketone. More preferred fluorinated ketones have a total of 4 to 8 carbon atoms. Representative examples of perfluorinated ketone compounds suitable for use in the processes and compositions of the invention include $CF_3CF_2C(O)CF(CF_3)_2$, $(CF_3)_2CFC(O)CF(CF_3)_2$, $CF_3(CF_2)_2C(O)CF(CF_3)_2$, $CF_3(CF_2)_3C(O)CF(CF_3)_2$, $CF_3(CF_2)_5C(O)CF_3$, $CF_3CF_2C(O)CF_2CF_2CF_3$, $CF_3C(O)CF(CF_3)_2$ and perfluorocyclohexanone.

In addition to demonstrating excellent fire-fighting performance, the fluorinated ketones offer important benefits in environmental friendliness and can offer additional important benefits in toxicity. For example, $CF_3CF_2C(O)CF(CF_3)_2$ has low acute toxicity, based on short term inhalation tests with mice exposed for four hours at a concentration of 50,000 ppm in air. Based on photolysis studies at 300 nm, $CF_3CF_2C(O)CF(CF_3)_2$ has an estimated atmospheric lifetime of 3 to 5 days. Other fluorinated ketones show similar absorbances and are expected to have similar atmospheric lifetimes. As a result of their rapid degradation in the lower atmosphere, the perfluorinated ketones have short atmospheric lifetimes and would not be expected to contribute significantly to global warming.

Fluorinated ketones can be prepared by known methods, e.g., by dissociation of perfluorinated carboxylic acid esters by reacting the perfluorinated ester with a source of fluoride ion under reacting conditions, as described in U.S. Pat. No. 5,466,877 (Moore et al.), by combining the ester with at least one initiating reagent selected from the group consisting of gaseous, non-hydroxylic nucleophiles; liquid, non-hydroxylic nucleophiles; and mixtures of at least one non-hydroxylic nucleophile (gaseous, liquid, or solid) and at least one solvent which is inert to acylating agents. The fluorinated carboxylic acid ester precursors can be derived from the corresponding fluorine-free or partially fluorinated hydrocarbon esters by direct fluorination with fluorine gas as described in U.S. Pat. No. 5,399,718 (Costello et al.).

Fluorinated ketones that are alpha-branched to the carbonyl group can be prepared as described in, for example, U.S. Pat. No. 3,185,734 (Fawcett et al.) and J. Am. Chem. Soc., v. 84, pp. 4285–88, 1962. These branched fluorinated ketones are most conveniently prepared by hexafluoropropylene addition to acyl halides in an anhydrous environment in the presence of fluoride ion at an elevated temperature, typically at around 50 to 80° C. The diglyme/fluoride ion mixture can be recycled for subsequent fluorinated ketone preparations, e.g., to minimize exposure to moisture. When this reaction scheme is employed, a small amount of hexafluoropropylene dimer and/or trimer may reside as a by-product in the branched perfluoroketone product. The amount of dimer and/or trimer may be minimized by gradual addition of hexafluoropropylene to the acyl halide over an extended time period, e.g., several hours. These dimer and/or trimer impurities can usually be removed by distillation from the perfluoroketone. In cases where the boiling points are too close for fractional distillation, the dimer and/or trimer impurity may be conveniently removed in an oxidative fashion by treating the reaction product with a mixture of an alkali metal permanganate in a suitable organic solvent such as acetone, acetic acid, or a mixture thereof at ambient or elevated temperatures, preferably in a sealed vessel. Acetic acid is a preferred solvent for this purpose; it has been observed that acetic acid tends not to degrade the ketone whereas in some instances some degradation of the ketone was noted when acetone was used. The oxidation reaction is preferably carried out at an elevated temperature, i.e., above room temperature, preferably from about 40° C. or higher, to accelerate the reaction. The reaction can be carried out under pressure, particularly if the ketone is low boiling. The reaction is preferably carried out with agitation to facilitate complete mixing of two phases which may not be totally miscible.

When relatively volatile, short-chain acyl halides are employed (e.g., acyl halides containing from two to about five carbon atoms) in the hexafluoropropylene addition reaction, significant pressure build-up can occur in the reactor at elevated reaction temperatures (e.g., at temperatures ranging from about 50° C. to about 80° C.). It has been discovered that this pressure build-up can be minimized if only a fraction of the acyl halide charge (e.g., about 5 to 30 percent) is initially added to the reactor and the remaining portion of acyl halide is co-charged with the hexafluoropropylene continuously or in small increments (preferably in an equimolar ratio) over an extended time period (e.g., 1 to 24 hours, depending in part upon the size of the reactor). The initial acyl halide charge and the subsequent co-feeding to the reactor also serves to minimize the production of by-product hexafluoropropylene dimers and/or trimers. The acyl halide is preferably an acyl fluoride and may be perfluorinated (e.g., $CF_3COF$, $C_2F_5COF$, $C_3F_7COF$), may be partially fluorinated (e.g., $HCF_2CF_2COF$), or may be unfluorinated (e.g., $C_2H_5COF$), with the product ketone formed being perfluorinated or partially fluorinated. The perfluoroketones may also include those that contain one or more catenated heteroatoms interrupting the carbon backbone in the perfluorinated portion of the molecule, such as, for example, a nitrogen, oxygen or sulfur atom.

Perfluorinated ketones which may be linear can be prepared according to the teachings of U.S. Pat. No. 4,136,121

(Martini et al.) by reacting a perfluorocarboxylic acid alkali metal salt with a perfluorinated acid fluoride. Such ketones can also be prepared according to the teachings of U.S. Pat. No. 5,998,671 (Van Der Puy) by reacting a perfluorocarboxylic acid salt with a perfluorinated acid anhydride in an aprotic solvent at elevated temperatures.

All of the above-mentioned patents describing the preparation of fluorinated ketones are incorporated by reference in their entirety.

The extinguishing process of the invention can be carried out by introducing a non-flammable extinguishing composition comprising at least one fluorinated ketone compound to a fire or flame. The fluorinated ketone compound(s) can be utilized alone or in a mixture with each other or with other commonly used clean extinguishing agents, e.g., hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, hydrobromocarbons, iodofluorocarbons, and hydrobromofluorocarbons. Such co-extinguishing agents can be chosen to enhance the extinguishing capabilities or modify the physical properties (e.g., modify the rate of introduction by serving as a propellant) of an extinguishing composition for a particular type (or size or location) of fire and can preferably be utilized in ratios (of co-extinguishing agent to fluorinated ketone compound(s)) such that the resulting composition does not form flammable mixtures in air. Preferably, the extinguishing mixture contains from about 10–90% by weight of at least one fluorinated ketone and from about 90–10% by weight of at least one co-extinguishing agent. Preferably, the fluorinated ketone compound(s) used in the composition have boiling points in the range of from about 0° C. to about 150° C., more preferably from about 0° C. to about 110° C.

The extinguishing composition can preferably be used in either the gaseous or the liquid state (or both), and any of the known techniques for introducing the composition to a fire can be utilized. For example, a composition can be introduced by streaming, e.g., using conventional portable (or fixed) fire extinguishing equipment; by misting; or by flooding, e.g., by releasing (using appropriate piping, valves, and controls) the composition into an enclosed space surrounding a fire or hazard. The composition can optionally be combined with inert propellant, e.g., nitrogen, argon, or carbon dioxide, to increase the rate of discharge of the composition from the streaming or flooding equipment utilized. When the composition is to be introduced by streaming or local application, fluorinated ketone compound(s) having boiling points in the range of from about 20° C. to about 110° C. (especially fluorinated ketone compounds which are liquid under ambient conditions) can preferably be utilized. When the composition is to be introduced by misting, fluorinated ketone compound(s) having boiling points in the range of from about 20° C. to about 110° C. are generally preferred. And, when the composition is to be introduced by flooding, fluorinated ketone compound(s) having boiling points in the range of from about 0° C. to about 75° C. (especially fluorinated ketone compound(s) which are gaseous under ambient conditions) are generally preferred.

Preferably, the extinguishing composition is introduced to a fire or flame in an amount sufficient to extinguish the fire or flame. One skilled in the art will recognize that the amount of extinguishing composition needed to extinguish a particular fire will depend upon the nature and extent of the hazard. When the extinguishing composition is to be introduced by flooding, cup burner test data (e.g., of the type described in the Examples, infra) can be useful in determining the amount or concentration of extinguishing composition required to extinguish a particular type and size of fire.

This invention also provides an extinguishing composition comprising (a) at least one fluorinated ketone compound; and (b) at least one co-extinguishing agent selected from the group consisting of hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, iodofluorocarbons, hydrobromofluorocarbons, and hydrobromocarbons. Representative examples of co-extinguishing agents which can be used in the extinguishing composition include $CF_3CH_2CF_3$, $C_5F_{11}H$, $C_6F_{13}H$, $C_4F_9H$, $CF_3CFHCFHCF_2CF_3$, $H(CF_2)_4H$, $CF_3H$, $C_2F_5H$, $CF_3CFHCF_3$, $CF_3CF_2CF_2H$, $CF_3CHCl_2$, $CF_3CHClF$, $CF_3CHF_2$, $CF_4$, $C_2F_6$, $C_3F_8$, $C_4F_{10}$, $C_6F_{14}$, $C_3F_7OCH_3$, $C_4F_9OCH_3$, $F(C_3F_6O)CF_2H$, $F(C_3F_6O)_2CF_2H$, $HCF_2O(CF_2CF_2O)CF_2H$, $HCF_2O(CF_2CF_2O)_2CF_2H$, $HCF_2O(CF_2O)(CF_2CF_2O)CF_2H$, $C_2F_5Cl$, $CF_3Br$, $CF_2ClBr$, $CF_3I$, $CF_2HBr$, n-$C_3H_7Br$, and $CF_2BrCF_2Br$. (For a representative listing of known clean extinguishing agents, see NFPA 2001, "Standard for Clean Agent Fire Extinguishing Systems," 2000 Edition, Table 1–5.1.2, p. 2001–5.) The ratio of co-extinguishing agent to fluorinated ketone is preferably such that the resulting composition does not form flammable mixtures in air (as defined by standard test method ASTM E681–85). The weight ratio of co-extinguishing agent to fluorinated ketone may vary from about 9:1 to about 1:9.

These fluorinated ketone compositions can be utilized in co-application processes with not-in-kind fire-fighting technologies to provide enhanced extinguishing capabilities. For example, the liquid composition $CF_3CF_2C(O)CF(CF_3)_2$ can be introduced into an aqueous film forming foam (AFFF) solution stream, for example, utilizing a Hydro-Chem™ nozzle manufactured by Williams Fire & Hazard Control, Inc., Mauriceville, Tex. to give the AFFF three-dimensional fire-fighting capability. The AFFF can carry the $CF_3CF_2C(O)CF(CF_3)_2$ a much longer distance than it could be delivered by itself to a remote three dimensional fuel fire, allowing the $CF_3CF_2C(O)CF(CF_3)_2$ to extinguish the three-dimensional fuel fire where the AFFF stream by itself would not.

Another co-application process utilizing fluorinated ketones can be extinguishing a fire using a combination of a gelled halocarbon with dry chemical. A dry chemical can be introduced in suspension in the liquid $CF_3CF_2C(O)CF(CF_3)_2$ and discharged from a manual handheld extinguisher or from a fixed system.

Yet another co-application process utilizing fluorinated ketones is the process where the fluorinated ketone is super-pressurized upon activation of a manual hand-held extinguisher or a fixed system using an inert off-gas generated by the rapid burning of an energetic material such as glycidyl azide polymer. In addition, rapid burning of an energetic material such as glycidyl azide polymer that yields a hot gas can be used to heat and gasify a liquid fluorinated ketone of the invention or other liquid fire extinguishing agent to make it easier to disperse. Furthermore, an unheated inert gas (e.g., from rapid burning of an energetic material) might be used as to propel liquid fluorinated ketones of the invention or other liquid fire extinguishing agents to facilitate dispersal.

The above-described fluorinated ketone compounds can be useful not only in controlling and extinguishing fires but also in preventing the combustible material from igniting. The invention thus also provides a process for preventing fires or deflagration in an air-containing, enclosed area which contains combustible materials of the self-sustaining or non-self-sustaining type. The process comprises the step of introducing into an air-containing, enclosed area a non-flammable extinguishing composition which is essentially gaseous, i.e., gaseous or in the form of a mist, under use conditions and which comprises at least one fluorinated ketone compound containing up to two hydrogen atoms, optionally up to two halogen atoms selected from chlorine, bromine, iodine, and a mixture thereof, and optionally containing additional catenated heteroatoms, and the composition being introduced and maintained in an amount sufficient to impart to the air in the enclosed area a heat capacity per mole of total oxygen present that will suppress combustion of combustible materials in the enclosed area.

Introduction of the extinguishing composition can generally be carried out by flooding or misting, e.g., by releasing (using appropriate piping, valves, and controls) the composition into an enclosed space surrounding a fire. However, any of the known methods of introduction can be utilized provided that appropriate quantities of the composition are metered into the enclosed area at appropriate intervals. Inert propellants, such as those propellants generated by decomposition of energetic materials such as glycidyl azide polymers, can optionally be used to increase the rate of introduction.

For fire prevention, fluorinated ketone compound(s) (and any co-extinguishing agent(s) utilized) can be chosen so as to provide an extinguishing composition that is essentially gaseous under use conditions. Preferred compound(s) have boiling points in the range of from about 0° C. to about 110° C.

The composition is introduced and maintained in an amount sufficient to impart to the air in the enclosed area a heat capacity per mole of total oxygen present that will suppress combustion of combustible materials in the enclosed area. The minimum heat capacity required to suppress combustion varies with the combustibility of the particular flammable materials present in the enclosed area. Combustibility varies according to chemical composition and according to physical properties such as surface area relative to volume, porosity, etc.

In general, a minimum heat capacity of about 45 cal/° C. per mole of oxygen is adequate to extinguish or protect moderately combustible materials (e.g., wood and plastics), and a minimum of about 50 cal/° C. per mole of oxygen is adequate to extinguish or protect highly combustible materials (e.g., paper, cloth, and some volatile flammable liquids). Greater heat capacities can be imparted if desired but may not provide significantly greater fire suppression for the additional cost involved. Methods for calculating heat capacity (per mole of total oxygen present) are well-known (see, e.g., the calculation described in U.S. Pat. No. 5,040,609 (Dougherty et al.), the description of which is incorporated herein by reference in its entirety).

The fire prevention process of the invention can be used to eliminate the combustion-sustaining properties of air and to thereby suppress the combustion of flammable materials (e.g., paper, cloth, wood, flammable liquids, and plastic items). The process can be used continuously if a threat of fire always exists or can be used as an emergency measure if a threat of fire or deflagration develops.

Objects and advantages of this invention are further illustrated by the following examples, but the particular materials and amounts thereof recited in these examples, as well as other conditions and details, should not be construed to unduly limit this invention. Unless otherwise specified, all percentages and proportions are by weight.

EXAMPLES

Example 1

$CF_3CF_2C(O)CF(CF_3)_2$— 1,1,1,2,4,4,5,5,5-nonafluoro-2-trifluoromethyl-butan-3-one Into a clean dry 600 mL Parr reactor equipped with stirrer, heater and thermocouple were added 5.6 g (0.10 mol) of anhydrous potassium fluoride and 250 g of anhydrous diglyme (anhydrous diethylene glycol dimethyl ether, available from Sigma Aldrich Chemical Co. used in all subsequent syntheses). The anhydrous potassium fluoride used in this synthesis, and in all subsequent syntheses, was spray dried, stored at 125° C. and ground shortly before use. The contents of the reactor were stirred while 21.0 g (0.13 mol) of $C_2F_5COF$ (approximately 95.0 percent purity) was added to the sealed reactor. The reactor and its contents were then heated, and when a temperature of 70° C. had been reached, a mixture of 147.3 g (0.98 mol) of $CF_2{=}CFCF_3$ (hexafluoropropylene) and 163.3 g (0.98 mol) of $C_2F_5COF$ was added over a 3.0 hour time period. During the addition of the hexafluoropropylene and the $C_2F_5COF$ mixture, the pressure was maintained at less than 95 psig (7500 torr). The pressure at the end of the hexafluoropropylene addition was 30 psig (2300 torr) and did not change over the 45-minute hold period. The reactor contents were allowed to cool and were one-plate distilled to obtain 307.1 g containing 90.6% 1,1,1,2,4,4,5,5,5-nonafluoro-2-trifluoromethyl-butan-3-one and 0.37% $C_6F_{12}$ (hexafluoropropylene dimer) as determined by gas chromatography. The crude fluorinated ketone was water-washed, distilled, and dried by contacting with silica gel to provide a fractionated fluorinated ketone of 99% purity and containing 0.4% hexafluoropropylene dimers.

Example 1A

A fractionated fluorinated ketone made according to the same procedures as in Example 1 was purified of dimers using the following procedure. Into a clean dry 600 mL Parr reactor equipped with stirrer, heater and thermocouple were added 61 g of acetic acid, 1.7 g of potassium permanganate, and 301 g of the above-described fractionated 1,1,1,2,4,4,5,5,5-nonafluoro-2-trifluoromethyl-butan-3-one. The reactor was sealed and heated to 60° C., while stirring, reaching a pressure of 12 psig (1400 torr). After 75 minutes of stirring at 60° C., a liquid sample was taken using a dip tube, the sample was phase split and the lower phase was washed with water. The sample was analyzed using glc and showed undetectable amounts of hexafluoropropylene dimers and small amounts of hexafluoropropylene trimers. A second sample was taken 60 minutes later and was treated similarly. The glc analysis of the second sample showed no detectable dimers or trimers. The reaction was stopped after 3.5 hours, and the purified ketone was phase split from the acetic acid and the lower phase was washed twice with water. 261 g of the ketone was collected, having a purity greater than 99.6% by glc and containing no detectable hexafluoropropylene dimers or trimers.

Example 1B

The following example was run to demonstrate the use of $KMnO_4$/acetic acid to purify $C_2F_5COCF(CF_3)_2$, made according to the teachings set forth in Example 1, which contained a high concentration (about 5%) of hexafluoropropylene dimers.

Into a clean dry 600 mL Parr reactor equipped with a stirrer, heater and thermocouple were added 60 g of acetic acid, 30 g of potassium permanganate and 286 g of the fluorinated ketone, $C_2F_5COCF(CF_3)_2$ (94% purity, containing about 5.2% dimers of hexafluoropropylene). The contents of the reactor were held at 60° C. for 25 hours to ensure that all of the dimers had been oxidized. While holding at 60° C., the reactor pressure continued to rise until a final pressure of 70 psig (4400 torr) was reached. The fluorinated ketone was distilled from the acetic acid, 255 g was collected, and the distilled ketone was washed twice with water. Ultimately, 242 g of the ketone was collected, having a purity of greater than 99.1% with no detectable hexafluoropropylene dimers or trimers (by glc).

Example 1C

The following example was run to demonstrate the use of $KMnO_4$/acetone to purify $C_2F_5COCF(CF_3)_2$, made according to the teachings set forth in Example 1, which contained a very high concentration (about 20%) of hexafluoropropylene dimers.

A two liter three-necked round bottom flask was equipped with an overhead air stirrer, water condenser and addition funnel. 360 g of acetone and 78 g (0.49 mol) of potassium permanganate were placed in the flask and the contents cooled to about 18° C. 357 g (0.90 mol) of $C_2F_5COCF(CF_3)_2$ (80% purity and containing about 20% hexafluoropropylene dimers, made according to the general procedure described in Example 1), was added slowly dropwise to the cooled contents. After the addition was complete, the resulting solution was stirred for about two hours at room temperature. A small amount (about 10 nL) of water was added, followed by the addition of just enough aqueous saturated sodium bisulfite solution to completely decolorize the acetone solution and dissolve the brown manganese dioxide precipitate. Additional water was added to give a clean phase separation, and the lower phase was separated and washed again with an equal volume of water to give 138 g of product. This product was combined with the product of an earlier experiment (198 g), and the combined product, which still contained acetone, was treated with 80 mL of concentrated sulfuric acid by addition of the acid through the top of a water cooled condenser to the product contained in a water bath-cooled round bottom flask. The ketone was then distilled from the combined product/sulfuric acid mixture as an azeotrope with the residual acetone. The resulting distillate contained two phases which were separated, and the lower phase was washed again with deionized water to provide 138 g of $C_2F_5COCF(CF_3)_2$ in a purity of 99.7% and which contained no hexafluoropropylene dimers nor any acetone as determined by glc.

Example 2

$(CF_3)_2CFC(O)CF(CF_3)_2$— 1,1,1,2,4,5,5,5,6,6,6-octafluoro-2,4-bis(trifluoromethyl)pentan-3-one 8.1 g (0.14 mol) of anhydrous potassium fluoride, 216 g (0.50 mol) of perfluoro(isobutyl isobutyrate) and 200 grams of anhydrous diglyme were charged to a clean dry 600 mL Parr pressure reactor. After cooling the reactor to <0° C., 165 g (1.10 mol) of hexafluoropropylene was added to the resulting mixture. The contents in the reactor were allowed to react overnight at 70° C. with stirring, then the reactor was allowed to cool and the excess pressure in the reactor was vented to the atmosphere. The contents of the reactor were then phase split to obtain 362.5 g of lower phase. The lower phase was retained and mixed with lower phases saved from previous analogous reactions. To 604 g of accumulated lower phases containing 22% perfluoroisobutyryl fluoride and 197 g (1.31 mol) of hexafluoropropylene was added 8 g (0.1 mol) of anhydrous potassium fluoride and 50 g of anhydrous diglyme, and the resulting mixture was allowed to react in the Parr reactor in the same manner as before. This time 847 g of lower phase resulted, containing 54.4% desired material and only 5.7% perfluoroisobutyryl fluoride. The lower phase was then water washed, dried with anhydrous magnesium sulfate, and fractionally distilled to give 359 g of 1,1,1,2,4,5,5,5,6,6,6-octafluoro-2,4-bis(trifluoromethyl)pentan-3-one having 95.2% purity as determined by gas chromatography and mass spectroscopy ("gcms") (47% theoretical yield) and having a boiling point of 73° C.

Example 3

65% $(CF_3)_2CFC(O)CF(CF_3)_2$, 35% $CF_3CF_2CF_2C(O)CF(CF_3)_2$—a blend of compounds from Examples 2 and 7, respectively

Example 4

$CF_3CF_2CF_2CF_2CF_2CF_2C(O)CF_3$— 1,1,1,3,3,4,4,5,5,6,6,7,7,8,8,8-hexadecafluorooctan-2-one 1052 mL of 2-octyl acetate was converted to the perfluorinated ester via direct fluorination as described in U.S. Pat. No. 5,488,142 (Fall et al.). The resulting perfluorinated ester was treated with methanol to convert it to the hemiketal to allow distillation of the reaction solvent. 1272 g of the resulting hemiketal was slowly added to 1200 mL of concentrated sulfuric acid, and the resulting reaction mixture was re-fractionated to yield 1554.3 g of 1,1,1,3,3,4,4,5,5,6,6,7,7,8,8,8-hexadecafluoro-octan-2-one, having a boiling point of 97° C. and having a purity of 98.4% as measured by nuclear magnetic resonance spectroscopy.

Example 5

$CF_3C(O)CF(CF_3)_2$— 1,1,1,3,4,4,4-heptafluoro-3-trifluoromethylbutan-2-one

A mixture consisting of 421 g of trifluoroacetic anhydride, 319.5 g of anhydrous diglyme, 131 g of anhydrous potassium fluoride and 315 g of hexafluoropropylene was heated in a 3-liter HASTELLOY™ (Haynes, Inc., Kokomo, Ind.) pressure vessel under autogenous pressure at 50° C. for 16 hours. The gaseous product was fractionally distilled to give 319.1 g of 1,1,1,3,4,4,4-heptafluoro-3-trifluoromethyl-butan-2-one having a boiling point of 25° C. Purity was 99.6% as determined by gas chromatography. The structure was verified using nuclear magnetic resonance spectroscopy.

Example 6

$HCF_2CF_2C(O)CF(CF_3)_2$— 1,1,1,2,4,4,5,5-octafluoro-2-trifluoromethylpentan-3-one Into a one liter three-necked round bottom flask equipped with an overhead stirrer, condenser and addition funnel were charged 315 g (1.07 mol) of potassium dichromate and 442 g of water. To this mixture was added 212 g of concentrated sulfuric acid in portions so that the temperature of the reaction mixture reached 54° C. by the end of the acid addition. The reaction mixture was then heated to 88° C., and 141.2 g (1.07 mol) of tetrafluoropropanol was slowly added dropwise, which warmed the contents to 102° C. during the course of the addition. Following the addition the reaction temperature was held at 102° C. for two hours. The resulting aqueous solution was then separated into two portions, and each portion was extracted twice with about 170 g of diethyl ether. The two aqueous portions were recombined, and a final extraction of the entire aqueous solution was then carried out using 205 g of diethyl ether. The ether solution portions were combined and the combined portions were then neutralized and extracted by vigorous stirring with 100 g of 40% aqueous potassium hydroxide. The ether layer was discarded and the water was removed from the dark blue aqueous layer by heating at 50–60° C. under aspirator vacuum until nearly dry. Hexane was added and distilled off to azeotropically remove the last residue of water from the chromium salt. About 700 mL of denatured alcohol was added to the mixture, and the resulting mixture was heated to reflux for two hours with stirring. The residual chromium salts were removed from the alcohol solution via filtration, and the light yellow filtrate was evaporated to dryness. This filtrate residue was then carefully treated with concentrated sulfuric acid, and the resulting acid was removed by distillation from the sulfuric acid. 127 g of the acid, $HC_2F_4CO_2H$, was recovered having a boiling point of 132–134° C.

The entire recovered acid product was treated with 264 g (1.35 mol) of benzotrichloride, and the resulting mixture was heated to 70° C. for 19 hours. Some of the desired acid chloride product, $HC_2F_4C(O)Cl$, distilled from the reaction mixture during this time and was collected in an ice water-cooled trap. The contents of the trap were combined with the reaction mixture and were distilled to yield 70 g of acid chloride having 95% purity as determine by glc, and having a (C=O) stretch of 1795 $cm^{-1}$ as determined by infrared spectroscopy. This product was used without further purification in the next step.

In order to convert the carbonyl chloride to carbonyl fluoride, 65 g (0.375 mole) of $HC_2F_4C(O)Cl$ was added dropwise to 60 g of anhydrous sodium fluoride (dried at 125° C. for one hour) in 150 mL of freshly distilled anhydrous sulfolane at 60° C. During this dropwise addition the desired acid fluoride product distilled from the reaction mixture and was collected using a dry ice cooled condenser. After the end of the addition the flask was heated to 70° C. for one hour to complete the removal of the acid fluoride, resulting in the recovery of 35 g of $HC_2F_4C(O)F$ having greater than 99% purity as determined by glc.

The final ketone product, 1,1,1,2,4,4,5,5-octafluoro-2-trifluoromethylpentan-3-one, was prepared by fluoride-catalyzed addition of hexafluoropropylene to $HC_2F_4C(O)F$ using essentially the same procedure as described by R. D. Smith et al. in J. Am. Chem. Soc., 84, 4285 (1962). The resulting fluorinated ketone product had a boiling point of 70–71° C.

Example 7

$CF_3CF_2CF_2C(O)CF(CF_3)_2$— 1,1,1,2,4,4,5,5,6,6,6-undecafluoro-2-trifluoromethylhexan-3-one Into a clean dry 600 mL Parr reactor equipped with stirrer, heater and thermocouple were added 5.8 g (0.10 mol) of anhydrous potassium fluoride and 108 g of anhydrous diglyme. The contents of the reactor were stirred and cooled with dry ice while 232.5 g (1.02 mol) of n-$C_3F_7COF$ (approximately 95.0 percent purity) was added to the sealed reactor. The reactor and its contents were then heated, and when a temperature of 72° C. had been reached, 141 g (0.94 mol) of $CF_2{=}CFCF_3$ (hexafluoropropylene) was added at a pressure of 85 psig (5150 torr) over a 3.25 hour time period. During the addition of hexafluoropropylene the temperature of the reactor was increased slowly to 85° C. while maintaining the pressure at less than 90 psig (5400 torr). The pressure at the end of the hexafluoropropylene addition was 40 psig (2800 torr) and did not change over an additional 4-hour hold period. The lower phase was fractionally distilled to give 243.5 grams of 1,1,1,2,4,4,5,5,6,6,6-undecafluoro-2-trifluoromethylhexan-3-one, having a boiling point of 72.5° C. and a purity of 99.9% as determined by gas chromatography. The structure was confirmed by gcms.

Example 8

$(CF_3)_2CFC(O)CF_2Cl$—1-chloro-1,1,3,4,4,4-hexafluoro-3-trifluoromethyl-butan-2-one To a clean dry 600 mL Parr pressure reactor was charged 53.5 g (0.92 mol) of anhydrous potassium fluoride, 150 g of anhydrous diglyme and 150 g of chlorodifluoroacetic anhydride. With the reactor set at 80° C. and 92 psig (5500 torr), 123 g (0.820 mol) of hexafluoropropylene was charged over a 3 hour period at a tank pressure not exceeding 120 psig (7000 torr). Following reaction for ½ hour at 80° C., the reactor contents were allowed to cool and were distilled to obtain 180.6 g of crude material. Upon fractional distillation, acetic acid/$KMnO_4$ treatment and refractionation of the crude material, 46.1 g (26% of theoretical yield) of $(CF_3)_2CFC(O)CF_2Cl$, a clear colorless liquid, was obtained having a purity of 98.8% as determined by gas chromatography.

Example 9

$CF_3CF_2C(O)CF_2CF_2CF_3$— 1,1,1,2,2,4,4,5,5,6,6,6-dodecafluorohexan-3-one 545 g of 3-hexyl acetate was fluorinated using essentially the same procedure as described in U.S. Pat. No. 5,488,142 (Fall et al.). 1031 g of the resulting perfluorinated ester was then converted to the ketone, using essentially the same procedure as described in Example 13 (i.e., for the preparation of $CF_3C(O)CF_2CF_3$). The crude ketone was fractionally distilled from concentrated sulfuric acid to give 90 g of 1,1,1,2,2,4,4,5,5,6,6,6-dodecafluorohexan-3-one, having a boiling point of 50° C. and having a purity of 98.7% as determined by gcms.

Example 10

$CF_3C(O)CH_2C(O)CF_3$—1,1,1,5,5,5-hexafluoropentan-2,4-dione

This diketone is available from Sigma Aldrich Chemical Co.

Example 11

$(CF_3)_2CFC(O)C(O)CF(CF_3)_2$— 1,1,1,2,5,6,6,6-octafluoro-2,5-bis(trifluoromethyl)hexan-3,4-dione Perfluorodibutyl oxalate was prepared from direct fluorination of dibutyl oxalate using essentially the same procedure as described in U.S. Pat. No. 5,488,142 (Fall et al.). A mixture of 1002 g of perfluorodibutyl oxalate, 1008 g of anhydrous diglyme, 40.4 g of anhydrous potassium fluoride and 806 g of hexafluoropropylene was heated in a 3-liter HASTELLOY™ pressure vessel under autogenous pressure with stirring for 16 hours at 50° C. The resulting reaction product was fractionated to produce 1,1,1,2,5,6,6,6-octafluoro-2,5-bis-trifluoromethyl-hexan-3,4-dione, having a boiling point of 92° C. and having a purity of 93.4% as measured by gas chromatography and mass spectroscopy.

Example 12

$CF_3CF_2CF_2C(O)CF_2CF_2CF_3$— 1,1,1,2,2,3,3,5,5,6,6,7,7,7tetradecafluoroheptan-4-one This linear ketone can be prepared using essentially the same procedure as described in U.S. Pat. No. 4,136,121 (Martini et al.), for example, by reacting $CF_3CF_2CF_2COO^-K^+$ with $CF_3CF_2CF_2COF$ in tetraethylene glycol dimethyl ether for about 60 hours at a temperature of about 100° C.

Example 13

$CF_3C(O)CF_2CF_3$—1,1,1,3,3,4,4,4-octafluorobutan-2-one 1341 g of sec-butyl acetate was fluorinated using essentially the same procedure as described in U.S. Pat. No. 5,488,142 (Fall et al.). The resulting perfluorinated ester (688 g) was isolated from the reaction mixture by fractionation. The ester was then decomposed according to the method described by Moore in U.S. Pat. No. 5,466,877 wherein the ester was added dropwise to a 1-liter, 3-neck flask equipped with a magnetic stirrer, dry ice condenser and temperature probe containing 0.5 mL of pyridine. The pot temperature was maintained at about −10° C., during which time the conversion to the ketone occurred. The gaseous ketone product was fractionated to give 435 g. of 1,1,1,3,3,4,4,4-octafluoro-butan-2-one, having a boiling point of 0° C., with purity of 99.7% as determined by gas chromatography and mass spectroscopy.

Example 14

$CF_3OCF_2CF_2C(O)CF(CF_3)_2$— 1,1,2,2,4,5,5,5-octafluoro-1-trifluoromethoxy-4-trifluoromethylpentan-3-one Into a clean dry 600 mL Parr reactor were added 11.6 g (0.20 mol) of anhydrous potassium fluoride and 113.5 g of anhydrous diglyme. The contents of the reactor were stirred and cooled with dry ice, then 230 g (0.96 mol) of $CF_3OCF_2CF_2COF$ (approximately 97 percent purity) was added to the sealed reactor using isolated vacuum. With the reactor at 80° C. and pressure of 80 psig (4900 torr), 154 g (1.03 mol) of $CF_2{=}CFCF_3$ was gradually added over a 3½ hour time period. Following a one hour reaction hold time, the product was recovered from the reaction mixture by distillation and phase split prior to fractionation to give 100 g of 1,1,2,2,4,5,5,5-octafluoro-1-trifluoromethoxy-4-trifluoromethylpentan-3-one, having a boiling point of 77° C. and a purity of 99.8% as determined by gas chromatography. The structure was confirmed by gas chromatography and mass spectroscopy.

Example 15

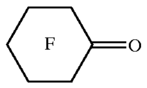

—decafluorocyclohexanone (perfluorocyclohexanone)

2500 mL of cyclohexyl acetate was converted to the perfluorinated ester via direct fluorination using 1,1,2-trichlorotrifluoroethane as the reaction medium as described in U.S. Pat. No. 5,399,718 (Costello et al.). Methanol was added to the reaction mixture to convert the perfluorinated ester to the corresponding hemiketal. The mixture was then fractionated to isolate the hemiketal from the 1,1,2-trichlorotrifluoroethane. 1686 g of the purified hemiketal was slowly added to 1800 mL of concentrated sulfuric acid and was re-fractionated to give 1054 g decafluorocyclohexanone having a boiling point of 53° C. and having a purity of greater than 95% as determined by gas chromatography (55.7% yield). The structure was confirmed by nuclear magnetic resonance spectroscopy.

Example 16

$CF_3CF_2CF_2CF_2C(O)CF(CF_3)_2$— 1,1,1,2,4,4,5,5,6,6,7,7,7-tridecafluoro-2-trifluoromethylheptan-3-one A mixture consisting of 775 g of perfluoropentanoyl fluoride, 800 g of anhydrous diglyme, 13.1 g of potassium fluoride, 17.8 g of anhydrous potassium bifluoride and 775 g of hexafluoropropylene was heated in a 3-liter stainless steel pressure vessel under autogeneous pressure at 50° C. for 16 hours. The product was fractionally distilled to give 413 g of 1,1,1,2,4,4,5,5,6,6,7,7,7-tridecafluoro-2-trifluoromethyl-heptan-3-one, having a boiling point of 97° C. and a 99.0% purity as determined by gas chromatography and mass spectroscopy.

Comparative Example C1

$CF_2ClBr$—bromochlorodifluoromethane

This manufacture of this product, commercially known as HALON™ 1211 fire extinguishing agent, was commercially phased out as of Jan. 1, 1994 in countries signatory to Montreal Protocol.

Comparative Example C2

$CF_3I$—iodotrifluoromethane

This compound is available as TRIODIDE™ fire extinguishing agent from Pacific Scientific, Carpinteria, Calif.

Comparative Example C3

$CF_3CH_2CF_3$—1,1,1,3,3,3-hexafluoropropane

This compound is available as FE-36™ fire extinguishing agent from E. I. duPont de Nemours & Co., Wilmington, Del.

Comparative Example C4

This mixture is an 80/20 blend of $CF_3CHCl_2$(HCFC-123 or 2,2-dichloro-1,1,1-trifluoroethane—available from Sigma Aldrich Chemical Co.) and $CF_4$ (tetrafluoromethane—available from Sigma Aldrich Chemical Co., Milwaukee, Wis.).

Comparative Example C5

$CF_3CFHCF_3$—1,1,1,2,3,3,3-heptafluoropropane

This compound is available as FM-200™ fire extinguishing agent from Great Lakes Chemical, West Lafayette, Ind.

Comparative Example C6

$CF_3CF_2CF_3$—perfluoro-n-propane

This compound is available as 3M™ CEA-308 fire extinguishing agent from 3M Company, St. Paul, Minn.

Comparative Example C7

$CF_3(CF_2)_2CF_3$—perfluoro-n-butane

This compound is available as 3M™ CEA-410 fire extinguishing agent from 3M Company.

Comparative Example C8

$CF_3(CF_2)_4CF_3$—perfluoro-n-hexane

This compound is available as 3M™ CEA-614 fire extinguishing agent from 3M Company.

Comparative Example C9

$CF_3CF(OCH_3)CF(CF_3)_2$— 1,1,1,2,3,4,4,4-octafluoro-3-trifluoromethyl-2-methoxybutane To a one liter round bottom flask equipped with an overhead stirrer, a condenser and an addition funnel was charged 12.8 g (0.22 mol) of anhydrous potassium fluoride, 106 g of anhydrous diglyme, 4 g of methyltrialkyl($C_8$–$C_{10}$) ammonium chloride (ADOGEN™ 464, available from Aldrich Chemical Company), 53.2 g (0.20 mol) of $CF_3C(O)CF(CF_3)_2$ (the perfluorinated ketone was prepared as described in Example 13), and 33.9 g (0.72 mol) of dimethyl sulfate. The resulting mixture was allowed to react at 40° C. for approximately 24 hours. Then approximately 25 g of a 50% aqueous potassium hydroxide solution was added to the reaction mixture, followed by 200 mL of water. The resulting crude product was azeotropically distilled from the reaction mixture. The lower phase of the resulting distillate was separated from the upper phase, was washed with water, was dried over anhydrous sodium sulfate, and was distilled (boiling point of 82–83° C.; yield of 45 g). The product identity, 2-methoxy-perfluoro(3-methylbutane), was confirmed by gcms and FTIR.

Comparative Example C10

$C_4F_9OCH_3$—perfluorobutyl Methyl Ether

This compound is available from 3M Company, St. Paul, Minn. as NOVEC™ HFE-7100 engineering fluid, which is an isomeric mixture of approximately 60% $(CF_3)_2CFCF_2OCH_3$ and approximately 40% $CF_3CF_2CF_2CF_2OCH_3$.

Comparative Example C11

$CF_3CF_2CF_2OCH_3$— 1,1,1,2,2,3,3-heptafluoro-3-methoxypropane

A jacketed one liter round bottom flask was equipped with an overhead stirrer, a solid carbon dioxide/acetone condenser, and an addition funnel. The flask was charged with 85 g (1.46 mol) of anhydrous potassium fluoride and 375 g of anhydrous diglyme, and the flask and its contents were then cooled to about −20° C. using a recirculating refrigeration system. 196 g (1.18 mol) of $C_2F_5COF$ was further added to the flask over a period of about one hour. The flask was then warmed to about 24° C., and 184.3 g (1.46 mol) of dimethyl sulfate was then added dropwise via the addition funnel over a 45 minute period. The resulting mixture was then stirred at room temperature overnight. A total of 318 mL water was then added dropwise to the mixture. The mixture was transferred to a one liter round bottom flask, and the resulting product ether was azeotropically distilled. The desired lower product phase of the resulting distillate was separated from the upper aqueous phase, was washed once with cold water, and was subsequently distilled to give 180 g of product (b.p. 36° C.; >99.9% purity by glc). The product identity, $CF_3(CF_2)_2OCH_3$, was confirmed by gcms and by $^1H$ and $^{19}F$ NMR.

Comparative Example C12

$(CF_3)_2CFC(O)CH_3$— 3,4,4,4-tetrafluoro-3-trifluoromethylbutan-2-one

To a clean dry 600 mL Parr pressure reactor was charged 3.5 g (0.060 mol) of anhydrous potassium fluoride and 110 g of anhydrous diglyme. The contents in the reactor were stirred and cooled to less than 0° C., and 25.0 g (0.403 mol) of acetyl fluoride, $CH_3C(O)F$, was charged from a cylinder. The reactor and its contents were then heated to 70° C., then 80.1 g (0.534 mol) of hexafluoropropylene was charged over a 6 hour period at a tank pressure not exceeding 55 psig (3600 torr) and preferentially less than 45 psig (3240 torr). After the reaction was allowed to proceed overnight at 70° C., the reactor contents were allowed to cool and were then distilled to obtain 85 g of material that contained 59% desired product. Upon fractional distillation there was obtained 24.0 g (28% of theoretical) of 3,4,4,4-tetrafluoro-3-trifluoromethylbutan-2-one, a clear colorless liquid boiling at 56° C. and having a purity of 97.8% as determined by gas chromatography and mass spectroscopy.

Comparative Example C13

$CF_3CF_2CF_2CF_2C(O)CH_3$—perfluorobutyl methyl ketone—available from Fluorochem USA (Catalog 00/01, Catalog number 6819), West Columbia, S.C.

Test Methods

Micro-Cup Burner Test

The Micro-Cup Burner Test is a laboratory test which measures the extinguishing ability of an agent based on the quantity of agent required to extinguish a fire under the following test conditions. The Micro-Cup Burner Test utilizes a quartz concentric-tube laminar-diffusion flame burner (micro-cup burner, of similar design to the above-described cup apparatus) aligned vertically with all flows upward. A fuel, typically propane unless otherwise specified, flows at 10.0 sccm (standard cubic centimeters per minute) through a 5-mm I.D. inner quartz tube which is centered in a 15-mm I.D. quartz chimney. The chimney extends 4.5 cm above the inner tube. Air flows through the annular region between the inner tube and the chimney at 1000 sccm. Prior to the addition of extinguishing composition, a visually stable flame is supported on top of the inner tube, and the resulting combustion products flow out through the chimney. An extinguishing composition to be evaluated is introduced into the air stream upstream of the burner. Liquid compositions are introduced by a syringe pump (which is calibrated to within 1%) and are volatilized in a heated trap. Gaseous compositions are introduced via a mass-flow controller to the air stream upstream from the burner. For consistency, the air-gaseous composition mixture then flows through the heated trap prior to its introduction to the flame burner. All gas flows are maintained by electronic mass-flow controllers which are calibrated to within 2%. The fuel is ignited to produce a flame and is allowed to burn for 90 seconds. After 90 seconds, a specific flow rate of composition is introduced, and the time required for the flame to be extinguished is recorded. The reported extinguishing concentrations are the recorded volume % of extinguishing composition in air required to extinguish the flame within an average time of 30 seconds or less.

Mass Ratio Calculation

The above-mentioned cup burner test measures the performance of an extinguishing composition by determining the minimum volume percent of composition in air required to extinguish a test fire. However, it is often desirable to directly compare the fire performance of an experimental extinguishing composition (e.g., a fluorinated ketone) against the performance of a state-of-the-art extinguishing composition, such as HALON™ 1211 fire extinguishing agent ($CF_2ClBr$, a bromochlorofluorocarbon). One way to make such a comparison is to derive the mass ratio of experimental composition to HALON™ 1211 fire extinguishing agent from the volume percentages of each composition required for extinguishing. The mass ratio can be calculated by dividing the experimental composition's extinguishing volume percent by the HALON™ 1211 agent's extinguishing volume percent and multiplying the resulting quotient (which, according to the ideal gas law, also represents the ratio of mole percents) times the weight average molecular weight of the experimental composition divided by the molecular weight of HALON™ 1211 agent (165 g/mole).

Testing

Examples 1–16 and Comparative Examples C1–C13

In Comparative Example C1, the extinguishing concentration (volume % in air) of HALON™ 1211 fire extinguishing agent was determined as using the Micro-Cup Burner Test.

In Examples 1–16, the extinguishing concentration of several perfluorinated ketones was also determined using the Micro-Cup Burner Test. The mass ratio as compared to HALON™ 1211 fire extinguishing agent was then calculated using the Mass Ratio Calculation.

In Comparative Examples C2–C11, various fluorinated extinguishing compositions known in the art (hydrofluorocarbons, perfluorocarbons, hydrochlorofluorocarbons, hydrofluoroethers, and iodofluorocarbons) were evaluated for their extinguishing concentration, and subsequently their mass ratios were calculated with respect to HALON™ 1211 agent.

In Comparative Examples C12–C13, two fluorinated ketones, each containing three hydrogen atoms on the carbon backbone, were evaluated for their extinguishing concentration and their mass ratio with respect to HALON™ 1211 agent.

Results from these evaluations are shown in TABLE 1 and are presented in ascending order of "Mass Ratio to HALON™ 1211," which represents the most meaningful clean extinguishing agent comparative performance parameter.

TABLE 1

| Ex. | Extinguishing Composition | Mol. Wt. | Boiling Point (° C.) | Ext. Conc. (vol %) | Mass Ratio to HALON ™ 1211 |
|---|---|---|---|---|---|
| C1 | $CF_2ClBr$ (HALON ™ 1211) | 165 | −3 | 3.6 | 1.00 |
| 1 | $CF_3CF_2C(O)CF(CF_3)_2$ | 316 | 47 | 3.5 | 1.86 |
| 2 | $(CF_3)_2CFC(O)CF(CF_3)_2$ | 366 | 71–72 | 3.3 | 2.03 |
| 3 | 65/35 (wt) ratio of $(CF_3)_2CFC(O)CF(CF_3)_2$ (Ex. 2) and $CF_3CF_2CF_2C(O)CF(CF_3)_2$ (Ex. 7) | 366 | 71–75 | 3.4 | 2.09 |
| 4 | $CF_3(CF_2)_5C(O)CF_3$ | 416 | 97 | 3.1 | 2.17 |
| 5 | $CF_3C(O)CF(CF_3)_2$ | 266 | 24 | 4.9 | 2.19 |
| 6 | $HCF_2CF_2C(O)CF(CF_3)_2$ | 298 | 70–71 | 4.4 | 2.20 |
| 7 | $CF_3(CF_2)_2C(O)CF(CF_3)_2$ | 366 | 73–75 | 3.6 | 2.21 |
| 8 | $(CF_3)_2CFC(O)CF_2Cl$ | 282.5 | 56 | 4.7 | 2.23 |
| 9 | $CF_3CF_2C(O)CF_2CF_2CF_3$ | 316 | 52 | 4.5 | 2.39 |
| 10 | $CF_3C(O)CH_2C(O)CF_3$ | 208 | 70–71 | 7.3 | 2.55 |
| 11 | $(CF_3)_2CFC(O)C(O)CF(CF_3)_2$ | 382 | 98 | 4.0 | 2.57 |
| 12 | $CF_3CF_2CF_2C(O)CF_2CF_2CF_3$ | 366 | 75 | 4.3 | 2.64 |
| 13 | $CF_3C(O)CF_2CF_3$ | 216 | 0 | 7.4 | 2.68 |
| 14 | $CF_3OCF_2CF_2C(O)CF(CF_3)_2$ | 382 | 77 | 4.3 | 2.76 |
| 15 | perfluorocyclohexanone | 278 | 53 | 6.0 | 2.80 |
| 16 | $CF_3(CF_2)_3C(O)CF(CF_3)_2$ | 416 | 97 | 4.3 | 3.00 |
| C2 | $CF_3I$ | 196 | −23 | 3.5 | 1.14 |
| C3 | $CF_3CH_2CF_3$ | 152 | −1 | 6.3 | 1.61 |
| C4 | $CF_3CHCl_2$ (80%) + $CF_4$ (20%) | 165 | −4 | 6.7 | 1.87 |
| C5 | $CF_3CHFCF_3$ | 170 | −16 | 6.6 | 1.90 |
| C6 | $CF_3CF_2CF_3$ | 188 | −37 | 6.5 | 2.05 |
| C7 | $CF_3(CF_2)_2CF_3$ | 238 | −2 | 5.3 | 2.12 |
| C8 | $CF_3(CF_2)_4CF_3$ | 338 | 56 | 4.0 | 2.27 |
| C9 | $CF_3CF(OCH_3)CF(CF_3)_2$ | 300 | 72–73 | 4.5 | 2.27 |
| C10 | $C_4F_9OCH_3$ | 250 | 61 | 6.1 | 2.52 |
| C11 | $CF_3(CF_2)_2OCH_3$ | 200 | 34 | 7.5 | 2.52 |
| C12 | $(CF_3)_2CFC(O)CH_3$ | 212 | 53–55 | 6.8 | 2.42 |
| C13 | $CF_3(CF_2)_3C(O)CH_3$ | 262 | 87 | 6.3 | 2.77 |

The data in TABLE 1 show that the extinguishing concentrations and mass ratios of perfluorinated ketones of this invention (see Examples 1–16) generally exhibit good performance as extinguishing compositions when compared to clean agent extinguishing compositions being evaluated as HALON™ fire extinguishing agent replacements (see Comparative Examples C2–C11).

The data also demonstrate generally superior fire extinguishing performance of the perfluoroketones when compared to partially fluorinated ketones with approximately the same carbon number. For example $CF_3(CF_2)_5C(O)CF_3$ (Ex. 4) and $CF_3C(O)CF(CF_3)_2$ (Ex. 5), where the ketone ha trifluoromethyl group on one side of the carbonyl group and has a perfluorinated alkyl group of 3 or 6 carbons on the other side, both show a lower "Mass Ratio to HALON™ 1211" value (2.17 and 2.19, respectively) than do either $(CF_3)_2CFC(O)CH_3$ (Comp. Ex. C12) or $CF_3(CF_2)_3C(O)CH_3$ (Comp. Ex. C13), which showed "Mass Ratio to HALON™ 1211" values of 2.42 and 2.77, respectively, where the ketone has an unfluorinated methyl on one side of the carbonyl group and a perfluorinated alkyl group (straight or branched) of 4 carbons on the other side. Also, the perfluorinated $CF_3CF_2C(O)CF(CF_3)_2$ (Ex. 1) shows a lower "Mass Ratio to HALON™ 1211" value than does the monohydrido analogue, $HCF_2CF_2C(O)CF(CF_3)_2$ (Ex. 6) (1.86 compared to 2.20), though the monohydrido ketone outperformed the trihydrido ketones (Comp. Ex. C12 and C13).

Examples 17–18

These two examples were run to illustrate the fire performance of a fluorinated ketone of this invention, $CF_3CF_2C(O)CF(CF_3)_2$ (the fluorinated ketone as prepared in Example 1), using a manual suppression full-scale streaming test for a clean extinguishing agent.

For each example, a standard off-the-shelf Amerex 131b HALON™ 1211 handheld extinguisher was used to introduce the extinguishing composition to the fire. The extinguisher was equipped with a standard ½ in (1.3 cm) nominal diameter rubber hose with a clean extinguishing agent nozzle attached to the end. In each case, the composition was super-pressurized using dry nitrogen at 130–150 psi (900–1040 kPa). The only modification to the standard extinguisher apparatus was that the nozzle orifice used had a slightly larger diameter (0.277 in, 0.70 cm) than did the standard nozzle orifice (0.234 in, 0.60 cm).

Both fire extinguishing tests were run following essentially the same test procedures and conditions as outlined in UL Standard 711 for the 2B and 5B pan fire scenarios, as normally conducted for UL approval at Underwriters Laboratories, Inc., Northbrook, Ill. The only deviation from that test procedure was that the fire tests for these examples were conducted outside. The fire test pans for the respective fires were sized to be 2.5 times larger than the ultimate extinguisher rating. For example, a 2B UL-rated extinguisher rating requires a skilled firefighter to be able to extinguish a 5 $ft^2$ (0.46 $m^2$) fire, a 5B UL-rated extinguisher rating requires extinguishing a 12.5 $ft^2$(1.16 $m^2$) fire, etc. For both examples, the UL specified pans were 12 in (30 cm) deep, into which was introduced 4.0 in (10 cm) of water, onto which was introduced 2 in (5 cm) of commercial grade heptane for fuel, leaving a 6 in (15 cm) freeboard above the fuel surface. Each fire was allowed to pre-burn 60 seconds before extinguishing commenced, using an agent flow rate of 0.75–0.80 kg/sec. The discharge time for the extinguishing of the fire was recorded as was the amount of agent discharged.

Results from these evaluations are presented in TABLE 2.

TABLE 2

| Ex. | UL Fire Pan Used | Pre-Burn Time (sec) | Extinguished (Y/N)? | Discharge Time (sec) | Agent Discharged (kg) | Flow Rate (kg/sec) |
|---|---|---|---|---|---|---|
| 17 | UL 2B | 60 | Y | 3.5 | 2.59 | 0.74 |
| 18 | UL 5B | 60 | Y | 3.8 | 2.87 | 0.76 |

The data in TABLE 2 show that the fluorinated ketone performed well as a streaming agent for fire extinguishing.

Example 19

This example was run to evaluate the fire performance of a fluorinated ketone of this invention, $CF_3CF_2C(O)CF(CF_3)_2$ (the fluorinated ketone as prepared in Example 1), in a total flooding evaluation for a clean extinguishing agent.

For this evaluation, a 1.28 $m^3$ (0.915 m×0.915 m×1.525 m) steel reinforced polycarbonate "box" enclosure was used, into which a fixed piping system, normally designed to deliver a gaseous clean extinguishing agent, was filled instead with a composition that is liquid at room temperature and discharged into the "box" to extinguish a fire. Using this modified system and procedure, the liquid fluorinated ketone used, $CF_3CF_2C(O)CF(CF_3)_2$, could be discharged into the enclosure indirectly in the same manner as could a gaseous clean extinguishing agent and thus allow the liquid agent to extinguish an obstructed fire located remotely in the enclosure.

In this modified procedure, a Swagelok Whitey 2000 mL cylinder was filled with 1000 g of $CF_3CF_2C(O)CF(CF_3)_2$ and was super-pressurized with nitrogen to 50 psi (345 kPa). Attached to the bottom of the cylinder was a 0.25 in (0.6 cm) Swagelok Whitey SS1RFA-A stainless steel angle valve, to which was fixed 34 in (86.4 cm) of nominal 0.25 in (6.5 mm) piping arrangement, including a 0.25 in (6.5 mm) Jamesbury Clincher ¼-turn ball valve. The piping was connected to a Bete NF 0500 square edge orifice nozzle. The Bete nozzle was installed to discharge horizontally from a side wall of the box equidistant from two adjacent walls of the enclosure, at a point 35 cm down from the ceiling of the enclosure.

The fire testing procedure followed was essentially the same as that described in the Ohmic Heating Test performed by Hughes Associates, Inc., Baltimore, Md. (see section A-3–6 of the 2000 Edition of the National Fire Protection Association NFPA 2001, Standard for Clean Agent Fire Extinguishing Systems). The discharge time was approximately 50 seconds and extinguishing of the obstructed fire using $CF_3CF_2C(O)CF(CF_3)_2$ was achieved within 35 seconds from the beginning of agent discharge, indicating good performance as a flooding clean extinguishing agent.

Various modifications and alterations of this invention will become apparent to those skilled in the art without departing from the scope and spirit of this invention.

We claim:

1. A process for removing dimeric or trimeric by-products from a fluorinated ketone, which comprises the step of treating said fluorinated ketone with an alkali metal permanganate in a suitable organic solvent at ambient or elevated temperatures.

2. The process of claim 1, where the step is carried out in a sealed vessel.

3. The process of claim 1 wherein the organic solvent contains acetic acid.

4. The process of claim 3 wherein the treating is run at an elevated temperature.

* * * * *

UNITED STATES PATENT AND TRADEMARK OFFICE

CERTIFICATE OF CORRECTION

PATENT NO. : 6,630,075 B2
DATED : October 7, 2003
INVENTOR(S) : Behr, Frederick E.

It is certified that error appears in the above-identified patent and that said Letters Patent is hereby corrected as shown below:

Column 18,
Line 51, delete "ha" and insert in place thereof -- has a --.

Signed and Sealed this

Fifteenth Day of June, 2004

JON W. DUDAS
*Acting Director of the United States Patent and Trademark Office*